US008097243B2

(12) United States Patent
Donnelly et al.

(10) Patent No.: US 8,097,243 B2
(45) Date of Patent: Jan. 17, 2012

(54) MICROPARTICLE-BASED TRANSFECTION AND ACTIVATION OF DENDRITIC CELLS

(75) Inventors: John J. Donnelly, Moraga, CA (US); Kimberly S. Denis-Mize, Concord, CA (US); Gary S. Ott, Oakland, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 12/755,266

(22) Filed: Apr. 6, 2010

(65) Prior Publication Data

US 2010/0196339 A1    Aug. 5, 2010

Related U.S. Application Data

(62) Division of application No. 09/715,902, filed on Nov. 17, 2000, now Pat. No. 7,713,739.

(60) Provisional application No. 60/166,514, filed on Nov. 19, 1999, provisional application No. 60/146,391, filed on Jul. 29, 1999.

(51) Int. Cl.
*A61K 48/00* (2006.01)
*C12N 15/63* (2006.01)
*C12N 5/0783* (2010.01)
*C12N 5/0784* (2010.01)

(52) U.S. Cl. .................. 424/93.21; 424/93.71; 435/347; 435/455

(58) Field of Classification Search ............... 424/93.21, 424/93.71; 435/347, 455
See application file for complete search history.

(56) References Cited

U.S. PATENT DOCUMENTS

| | | | |
|---|---|---|---|
| 3,773,919 A | 11/1973 | Boswell et al. | |
| 4,767,628 A | 8/1988 | Hutchinson | |
| 5,134,122 A | 7/1992 | Orsolini | |
| 5,595,897 A | 1/1997 | Midoux et al. | |
| 5,648,095 A | 7/1997 | Illum et al. | |
| 5,783,567 A * | 7/1998 | Hedley et al. | 514/44 R |
| 5,788,963 A | 8/1998 | Murphy et al. | |
| 5,846,827 A | 12/1998 | Celis et al. | |
| 5,851,756 A | 12/1998 | Steinman et al. | |
| 5,853,719 A | 12/1998 | Nair et al. | |
| 5,951,988 A | 9/1999 | Littel-van den Hurk et al. | |
| 5,962,318 A | 10/1999 | Rooney et al. | |
| 5,962,320 A | 10/1999 | Robinson | |
| 6,734,014 B1 * | 5/2004 | Hwu et al. | 435/325 |

FOREIGN PATENT DOCUMENTS

| | | |
|---|---|---|
| WO | 94/02156 | 2/1994 |
| WO | 9412158 | 6/1994 |
| WO | 96/37216 | 11/1996 |
| WO | 97/02810 | 1/1997 |
| WO | 97/24447 | 7/1997 |
| WO | WO 97/24447 * | 7/1997 |
| WO | 98/33487 | 8/1998 |
| WO | 99/58694 | 11/1999 |
| WO | 00/06123 | 2/2000 |

OTHER PUBLICATIONS

Fattal et al. (1998) J. Controlled. Rel., vol. 53, 137-143.*
Scheicher et al., "Uptake of Microparticle-Adsorbed Protein Antigen by Bond Marrow-Derived Dendritic Cells Results in Up-Regulation of Interleukin-1α and Interleukin-12 p40/p35 and Triggers Prolonged, Efficient Antigen Prsentation" Eur. J. Immunol. 25:1566-1572, 1995.
Hedley et al., "Microspheres Containing Plasmid-Encoded Antigens Elicit Cytotoxic T-Cell Response" Nature Medicine 4(3):365-368, Mar. 1998.
Singh et al., "Cationic Microparticles: A Potent Deliver System for DNA Vaccines" Proc. Natl. Acad. Sci. 97(2):811-816, Jan. 18, 2000.
Denis-Mize et al., "Cationic Microparticles as a Delivery System for DNA Vaccines" Abstracts of the General Meeting of the American Society for Microbiology Session No. 214/D, Abstract D-224, May 24, 2000.
U.S. Appl. No. 09/015,652.
Steinman, R.M., "The Dentritic Cells System and Its Role in Immunogenicity", Ann. Rev. Immunol. 1991, 9:271.
Banchereau, J.B. et al., "Dendritic Cells and the Control of Immunity," Nature, 1998, 392:245.
Denis-Mize, KS et al., "Plasmid DNA adsorbed onto cationic microparticles mediates target gene expression and antigen presentation by dendritic cells," Gene Therapy (2000) 7, 2105-2112.
Singh M et al. "Cationic microparticles: A potent delivery system for DNA vaccines," Proc Natl Acad Sci USA, Jan. 18, 2000, vol. 97, No. 2, pp. 811-816.
Ciftci K. et al. "DNA-PLGA Microparticles: A Promising Delivery System for Cancer Gene Therapy," AAPS Annual Meeting Abstracts Oneline 1( ):1999.
Spahn et al. (1996) Proc. Am. Assoc. Canc. Res., vol. 37, 486-487.
Yang et al. (1999) Int. J. Cancer, vol. 83, 532-540.
Manickan et al. (1997) J. Leuk. Biol., vol. 61, 125-132.
Tuting et al. (1998) J. Immunol., vol. 160,1139-1147.
Andreas Lundqvist et al., "Nonviral and Viral Gene Transfer into Different Subsets of Human Dendritic Cells Yield Comparable Efficiency of Transfection," Journal of Immunology, vol. 25, No. 6, 2002, pp. 445-454.
D.T. O'Hagan et al., "Long-Term Antibody Responds in Mice Following Subcutaneous Immunization with Ovalbumin Entrapped in Biodegradable Microparticles," Vaccine, vol. 11, No. 9, 1993, pp. 965-969.
Awasthi S. Cox. Abstract of "Transfection of Murine Dendritic Cell Line (JAWS II) by a Nonviral Transfection Reagent," Biotechniques, vol. 35, No. 3, 2003, pp. 600-602, 604.

(Continued)

*Primary Examiner* — Anne Marie S Wehbe
(74) *Attorney, Agent, or Firm* — Helen Lee; David Bonham

(57) ABSTRACT

The present invention provides an effective method for the transfection of dendritic cells by non-viral methods. The present invention provides this benefit by incubating dendritic cells and a specified transfection agent. The transfection agent comprises a polynucleotide and microparticles, with the microparticles being comprised of biodegradable polymer and cationic detergent. The dendritic cells and transfection agent are incubated for a time sufficient to transfect the dendritic cells with the polynucleotide.

5 Claims, 4 Drawing Sheets

OTHER PUBLICATIONS

Shuichi Ando et al., "PLGA Microspheres Containign Plasmid DNA: Preservation of Supercoiled DNA via Cytotoxic Lymphocytes and Elicit Antitumor Immunity," Journal of Immunology, vol. 168, No. 5, 2002, pp. 2393-2401.

Elke Walter et al., "Microencapsulation of DNA Using Poly (DL-Lactide-CO-Glycolide): Stability Issues and Release Characteristics, "Journal of Controlled Release, vol. 61, 1999, pp. 361-374.

Shibagaki N. Udey, Abstract of "Dendritic Cells Transduced with Protein Antigens Induced Cytotoxic Lymphocytes and Elicit Antitumor Immunity," Journal of Immunology, vol. 168, No. 5, 2002, pp. 2393-2401.

P. Lenz et al., Abstract of "Necleoporation of Dendritic Cells: Efficient Gene Transfer by Electroporation into Human onocyte-Derived Dendritic Cells," FEBS Lett, vol. 538, No. 1-3, 2003, pp. 149-154.

Takashima A. Morita, Abstract of "Dendritic Cells in Genetic Immunization," Journal of Leukocyte Biology, vol. 66, No. 2, 1999, pp. 350-356.

L. Zhong et al., Abstract of "Recombinant Adenovirus Is an Efficient and Non-Perturbing Genetic Vector for Human Dendritic Cells", Eur. J. Immunol., vol. 29, No. 3, 1999, pp. 964-972.

E. Fattal et al., "Biodegradable polyalkylcyanoacrylate nanoparticles for the delivery of oligonucleotides" Journal of Controlled Release, 53 (1998) 137-143.

Karhumaki et al., "An Improved Enrichment method for functionally competent, highly purified peripheral blood dendritic cells and its application to HIV-infected blood samples" Clin Exp Immunol 1993; 91:482-488.

* cited by examiner

MICROPARTICLE-BASED TRANSFECTION AND ACTIVATION OF DENDRITIC CELLS

CROSS REFERENCE TO RELATED APPLICATIONS

This application is a divisional of U.S. application Ser. No. 09/715,902, filed Nov. 17, 1999, now U.S. Pat. No. 7,713,739 entitled MICROPARTICLE-BASED TRANSFECTION AND ACTIVATION OF DENDRITIC CELLS, which is a non-provisional of Provisional Application Ser. No. 60/166,514 filed Nov. 19, 1999, now expired, which are incorporated herein by reference in their entireties. This application is also related to Patent Application Ser. No. 60/146,391, filed Jul. 29, 1999, which is incorporated herein by reference in its entirety.

FIELD OF THE INVENTION

The present invention relates to compositions and methods of providing dendritic cells for immunotherapy in connection with, for example, viruses or tumors. In particular, the invention relates to methods for generating antigen presenting dendritic cells by transfection, allowing for, e.g., the activation and expansion of large numbers of viral- or tumor-antigen-specific T cells for use in adoptive cellular immunotherapy against viruses and tumors.

BACKGROUND OF THE INVENTION

The generation of an immune response involves the sensitization of helper (CD4+) ($T_H$) and cytotoxic (CD8+) (CTL) T cell subsets through their interaction with antigen presenting cells. Antigen presenting cells express major histocompatibility (MHC)-class I or class II molecules associated with antigenic fragments (i.e., specific amino acid sequences derived from an antigen which bind to MHC I and MHC II for presentation on the cell surface). The MHC in humans is also referred to as the HLA (human leukocyte antigen) complex. The sensitized CD4+ T cells produce lymphokines that participate in the activation of B cells as well as various T cell subsets. The sensitized CD8+ T cells increase in numbers in response to lymphokines and act to destroy cells that express the specific antigenic fragments associated with matching MHC-encoded class I molecules. In the course of a tumor or viral infection, cytotoxic T cells eradicate cells expressing tumor or virus associated antigens.

Dendritic cells (DCs) are thought to be the most potent antigen presenting cells of the immune system (reviewed in Steinman, R. M. 1991. The dendritic cells system and its role in immunogenicity. Ann. Rev. Immunol. 9:271; Banchereau, J. B. and R. M. Steinman. 1998. Dendritic cells and the control of immunity. Nature. 392:245). Given their broad spectrum of roles in initiating the immune response by internalizing and processing antigens, migrating to lymphoid organs, secreting cytokines, and expressing co-stimulatory molecules required for lymphocyte signaling, it is no surprise that dendritic cells are logical targets for clinical use (Banchereau, J. B. and R. M. Steinman. 1998. Dendritic cells and the control of immunity. Nature. 392:245). By targeting antigens into dendritic cells in vivo or exposing dendritic cells to antigen ex vivo, it may be possible to enhance the immunogenicity of vaccines by eliciting helper and cytotoxic T cells, antibodies, and IL-12 for prophylactic applications, or induce T cell mediated anti-tumor responses for cancer immunotherapy. Akbari, et al. have suggested that transfection and activation of dendritic cells are key events for immunity following DNA vaccination by scarification of the ear skin in mouse models (O. Akbari, N. P., S. Garcia, R. Tascon, D. Lowrie, and B. Stockinger. 1999. DNA vaccination: transfection and activation of dendritic cells as key events for immunity. J. Exp. Med. 189:169). Anti-tumor CTL activity and protection against lethal tumor challenge in mouse models have been demonstrated using cytokine-driven bone-marrow-derived dendritic cells (BMDCs) pulsed with tumor-associated peptides (J. I. Mayordomo, T. Z., W. J. Storkus. 1995. Bone marrow-derived dendritic cells pulsed with synthetic tumour peptides elicit protective and therapeutic anti-tumour immunity. Nature Med. 1:1297), and whole tumor lysates (R. C. Fields, K. S., and J. J. Mule'. 1998. Murine dendritic cells pulsed with whole tumor lysates mediate potent antitumor immune responses in vitro and in vivo. Proc. Natl. Acad. Sci. USA 95:9482) transferred by the subcutaneous route.

In vitro generation of dendritic cells has been optimized sufficiently so that genetic immunotherapy based on passive transfer of dendritic cells has become an attractive target for development (N. Romani, S. G., D. Brang. 1994. Proliferating dendritic cell progenitors in human blood. J. Exp. Med. 180:83). However, in vitro transfection efficiency of dendritic cells by non-viral methods has been extremely poor (J. F. Arthur, L. H. B., M. D. Roth, L. A. Bui, S. M. Kiertscher, R. Lau, S. Dubinett, J. Glaspy, W. H. McBride, and J. S. Economou. 1997. A comparison of gene transfer methods in human dendritic cells. Cancer Gene Ther. 4:17) and has limited progress toward effective dendritic-cell-based immunotherapy. While progress has been made by the use of electroporation, the efficiency of transfection is extremely low and results in substantial loss of cell viability (V. F. I. Van Tendeloo, H.-W. S., F. Lardon, GLEE Vanham, G. Nijs, M. Lenjou, L. Hendriks, C. Van Broeckhoven, A. Moulijn, I. Rodrigus, P. Verdonk, D. R. Van Bockstaele, and Z. N. Berneman. 1988. Nonviral transfection of distinct types of human dendritic cells: high efficiency gene transfer by electroporation into hematopoietic progenitor- but not monocyte-derived dendritic cells. Gene Ther. 5:700). To date, no purely chemical method has been shown to be effective.

Particulate carriers have been used in order to achieve controlled, parenteral delivery of therapeutic compounds. Such carriers are designed to maintain the active agent in the delivery system for an extended period of time. Examples of particulate carriers include those derived from polymethyl methacrylate polymers, as well as microparticles derived from poly(lactides) (see, e.g., U.S. Pat. No. 3,773,919), poly (lactide-co-glycolides), known as PLG (see, e.g., U.S. Pat. No. 4,767,628) and polyethylene glycol, known as PEG (see, e.g., U.S. Pat. No. 5,648,095). Polymethyl methacrylate polymers are nondegradable while PLG particles biodegrade by random nonenzymatic hydrolysis of ester bonds to lactic and glycolic acids, which are excreted along normal metabolic pathways.

For example, U.S. Pat. No. 5,648,095 describes the use of microspheres with encapsulated pharmaceuticals as drug delivery systems for nasal, oral, pulmonary and oral delivery. Slow-release formulations containing various polypeptide growth factors have also been described. See, e.g., International Publication No. WO 94/12158, U.S. Pat. No. 5,134,122 and International Publication No. WO 96/37216.

Particulate carriers have also been used with adsorbed or entrapped antigens in attempts to elicit adequate immune responses. Such carriers present multiple copies of a selected antigen to the immune system and promote trapping and retention of antigens in local lymph nodes. The particles can be phagocytosed by macrophages and can enhance antigen presentation through cytokine release. For example, commonly owned, co-pending application Ser. No. 09/015,652, filed Jan. 29, 1998, describes the use of antigen-adsorbed and antigen-encapsulated microparticles to stimulate cell-mediated immunological responses, as well as methods of making the microparticles.

In commonly owned provisional Patent Application 60/036,316, for example, a method of forming microparticles is disclosed which comprises combining a polymer with an organic solvent, then adding an emulsion stabilizer, such as polyvinyl alcohol (PVA), then evaporating the organic solvent, thereby forming microparticles. The surface of the microparticles comprises the polymer and the stabilizer. Polynucleotides such as DNA, polypeptides, and antigens may then be adsorbed on those surfaces. See also PCT US99/17308.

Commonly owned Provisional Application No. 60/146,391 discloses a method of forming microparticles with adsorbent surfaces that are capable of adsorbing a variety of macromolecules including polynucleotides. In one embodiment, the microparticles are comprised of both a polymer and a detergent. The microparticles are derived from a polymer, such as a poly($\alpha$-hydroxy acid), preferably, a poly(D,L-lactide-co-glycolide), a polyhydroxy butyric acid, a polycaprolactone, a polyorthoester, a polyanhydride, a polycyanoacrylate, and the like, and are formed with detergents, such as cationic, anionic, or nonionic detergents, which detergents may be used in combination. Cationic detergents disclosed are cetrimide (CTAB), benzalkonium chloride, DDA (dimethyl dioctodecyl ammonium bromide), DOTAP, and the like. It is noted that these microparticles yield improved adsorption of viral antigens, and provide for superior immune responses, as compared to microparticles formed by a process using only PVA.

Dendritic cells can capture antigen at peripheral sites via macropinocytosis using membrane ruffling, or may also internalize antigen by receptor-mediated processes involving Fc$\gamma$III, the mannose receptor, or the C-type lectin DEC-205 (reviewed in Lanzavecchia, A. 1996. Mechanisms of antigen uptake for presentation. *Curr. Op. Immunol.* 8:348). Thus, dendritic cells may be targeted by the capture of larger (>250 nm) particulate antigens by phagocytosis. Biodegradable polymer microspheres such as poly-lactide-co-glycolide (PLG) are readily internalized by phagocytic cells up to a diameter of 5 µm (Ikada, Y. T. et al. 1990. Phagocytosis of polymer microspheres by macrophages. *Adv. Polymer. Sci.* 94:107) and have been utilized as carriers for drug delivery systems.

Recently, Newman, et al. reported cytoplasmic delivery of Texas red labeled dextran encapsulated in PLGA microspheres following phagocytosis in mouse peritoneal macrophages (K. D. Newman, G. K., J. Miller, V. Chlumecky, J. Samuel. 1999. Cytoplasmic delivery of a fluorescent probe by poly(D,L lactic-co-glycolic acid) microspheres. In 1999 *AAPS Annual Meeting Abstracts Online*, vol. 1).

The application of synthetic biopolymers for nucleic acid delivery has proven advantageous by protecting DNA against nuclease degradation and increasing cellular uptake (C. Chavany, T. S.-B., T. Le Doan, F. Puisieux, P. Couvreur, and C. Helene. 1994. Adsorption of oligonucleotides onto polyisohexylcyanoacrylate nanoparticles protects them against nucleases and increases their cellular uptake. *Pharm. Res.* 11:1370).

Evidence for direct transfection of non professional antigen presenting cells mediated by PLG was recently reported by Ciftci and Su who found PLG microparticles containing a DNA:polycation complex provided controlled release of DNA and surfactant-enhanced uptake and gene expression in 293 and MCF-7 cells (K. Ciftci, J. S. 1999. DNA-PLGA microparticles: a promising delivery system for cancer gene therapy. In 1999 *AAPS Annual Meeting Abstracts Online*, vol. 1).

While polyalkylcyanoacrylate nanoparticles have been used to bind CTAB-oligonucleotide complexes to deliver antisense oligonucleotides to macrophage cell lines in vitro (C. Chavany, T. S.-B., T. Le Doan, F. Puisieux, P. Couvreur, and C. Helene. 1994. Adsorption of oligonucleotides onto polyisohexylcyanoacrylate nanoparticles protects them against nucleases and increases their cellular uptake. *Pharm. Res.* 11:1370; E. Fattal, C. V., I. Aynie, Y. Nakada, G. Lambert, C. Malvy, and P. Couvreur. 1998. Biodegradable polyalkylcyanoacrylate nanoparticles for the delivery of oligonucleotides. *J. Controlled Release* 53:137), these vehicles have not been shown to transfect dendritic cells with plasmids carrying recombinant genes.

Hence, there is a need in the art for an effective non-viral technique for the transfection of dendritic cells. While microparticle technology has been heretofore used for introduction of polynucleotides into cells, applicants are aware of no such technology having been used for the transfection of dendritic cells, which are notoriously resistant to transfection.

SUMMARY OF THE INVENTION

The present invention provides an effective method for the transfection of dendritic cells by non-viral methods. The present invention provides this benefit by incubating dendritic cells and a specified transfection agent. The transfection agent comprises polynucleotide and microparticles, with the microparticles being comprised of a biodegradable polymer and a cationic detergent. The dendritic cells and transfection agent are incubated for a time sufficient to transfect the dendritic cells with the polynucleotide.

For the transfecting agent, the cationic detergent preferably comprises CTAB or cetrimide, while the polymer preferable is a poly($\alpha$-hydroxy acid), for example, a poly(lactide), a copolymer of D,L-lactide and caprolactone, or a copolymer of D,L-lactide and glycolide or glycolic acid, such as poly(D,L-lactide-co-glycolide). In a further preferred embodiment, the polynucleotide is provided in the form of a plasmid. In still further preferred embodiments, the polynucleotide encodes an antigen associated with a virus, such as HIV, meningitis A, meningitis B or meningitis C, or a tumor.

The dendritic cells can originate from any available source, for example, the bone marrow or blood of a vertebrate subject, preferably a human subject. Dendritic cells can be cultured, for example, for about 5 to about 10 days prior to transfection, in the presence of appropriate growth factors, for example, GM-CSF.

The dendritic cells and transfecting agent are preferably incubated for about 24 hours under appropriate conditions.

In some embodiments of the present invention, an effective amount of the transfected dendritic cells of the present invention are administered to a vertebrate subject in need thereof. In other embodiments, T cells are first activated by the dendritic cells of the present invention and then administered to a vertebrate subject in need thereof. The dendritic cells and/or T cells may originate, for example, from the vertebrate subject or a healthy vertebrate subject MHC-matched to the vertebrate subject. The dendritic cells and or T cells may be administered parenterally to the vertebrate subject.

One advantage of the present invention is that polynucleotides can be efficiently internalized by dendritic cells.

Another advantage of the present invention is that gene expression can be effected within dendritic cells.

Yet another advantage of the present invention is that antigen can be processed and presented in connection with MHC molecules on the surface of dendritic cells.

Another advantage of the present invention is that polynucleotides can be rapidly internalized and expressed, with antigen presentation.

Still another advantage of the present invention is that the methods of the invention can be used, for example, in genetic immunotherapy or vaccination with relative safely. For instance, both cationic detergents, such as CTAB, and biodegradable polymers, such as PLG, have been utilized in biomedical applications. Moreover, the obvious safety concerns with the use of live viral vectors can be avoided (reviewed in Rock, S. R. et al. 1998. Fully mobilizing host defense: building better vaccines. *Nature Biotech.* 16:1025).

These and other embodiments and advantages will become readily apparent to those skilled in the art upon review of this specification and the claims set forth below.

BRIEF DESCRIPTION OF THE DRAWINGS

FIG. 3 also illustrates % viability (right y-axis, line series) of BMDCs that were incubated with varying concentrations of pCMV-gag plasmid DNA formulated on PLG-CTAB microparticles. Where appropriate, data points represent the average values and standard error of duplicate samples.

DETAILED DESCRIPTION OF THE INVENTION

Figure 1:
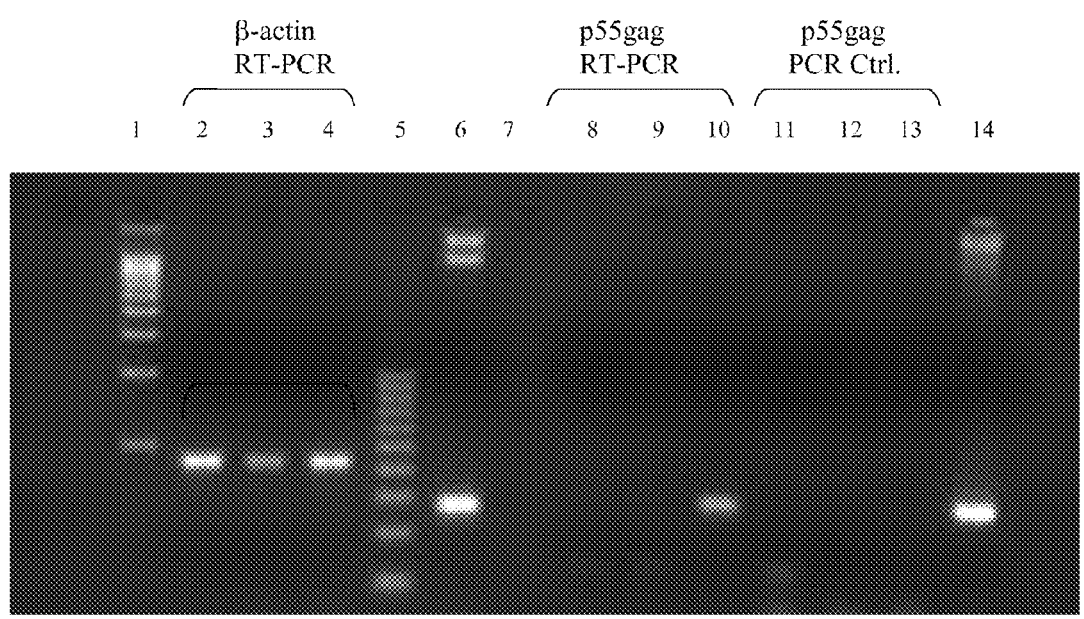
FIG. 1. Agarose gel electrophoresis of RT-PCR products for detection of target gene expression. Lane designations are as follows: 1) 500 bp DNA ladder, 2-4) β-actin control RT-PCR reactions from untreated, plasmid DNA, and PLG-CTAB-DNA treated bone-marrow-derived dendritic cells (BMDCs), 5) 100 bp DNA ladder, 6) untreated mRNA prep with control spike of pCMV-gag DNA, 8-10) p55gag RT-PCR from untreated, plasmid DNA, and PLG-CTAB-DNA treated BMDCs, 11-13) PCR negative control from untreated, plasmid DNA, and PLG-CTAB-DNA treated BMDCs, 14) pCMV-gag DNA PCR positive control.

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S., ed, CRC Press, 1997) and *Seymour/Carraher's Polymer Chemistry* (4th edition, Marcel Dekker Inc., 1996).

All publications, patents and patent applications cited herein, whether supra or infra, are hereby incorporated by reference in their entirety.

A. Definitions

In describing the present invention, the following terms will be employed, and are intended to be defined as indicated below.

The term "dendritic cells" is used herein to refer to antigen presenting cells characterized by their peculiar dendritic morphology and multiple thin-membrane projections, and by their high density of class II MHC molecules. Dendritic cells include Langerhans cells of the skin, "veiled cells" of afferent lymphatics, follicular dendritic cells, dendritic cells of the spleen, and interdigitating cells of lymphoid organs. Dendritic cells can be obtained from the skin, spleen, bone marrow, lymph nodes, other lymphoid organs, and peripheral blood cord blood. Preferably, dendritic cells are obtained from blood or bone marrow for use in the invention.

The term "microparticle" as used herein, refers to a particle of about 100 nm to about 150 μm in diameter, more preferably about 200 nm to about 30 μm in diameter, and most preferably about 500 nm to about 10 μm in diameter. Microparticle size is readily determined by techniques well known in the art, such as photon correlation spectroscopy, laser diffractometry and/or scanning electron microscopy.

Microparticles for use herein are preferably formed from materials that are preferable sterilizable, non-toxic and biodegradable. Such materials include, without limitation, poly (α-hydroxy acid), polyhydroxybutyric acid, polycaprolactone, polyorthoester, polyanhydride, PACA, and polycyanoacrylate. Preferably, microparticles for use with the present invention are derived from a poly(α-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, for example, in the case of the copolymers such as PLG, a variety of co-monomer (lactide:glycolide) ratios.

The term "cationic detergent" as used herein includes cationic surfactants and emulsion stabilizers. Cationic detergents include, but are not limited to, cetrimide, CTAB, benzalkonium chloride, DDA (dimethyl dioctodecyl ammonium bromide), Dioleoyl-3-Trimethylammonium-Propane (DOTAP), and the like.

A "polynucleotide" is a nucleic acid polymer. Polynucleotides according to the present invention are preferably of the minimum transfection unit length, which is on the order of about 1 kb. Furthermore, a "polynucleotide" can include both double- and single-stranded sequences, and can include naturally derived and synthetic DNA sequences. The term also includes sequences that include any of the known base analogs of DNA and RNA, and includes modifications, such as deletions, additions and substitutions (generally conservative in nature) to native sequences.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to native sequence.

By "antigen" is meant a molecule that contains one or more epitopes capable of stimulating an immunological response when the antigen is presented on a dendritic cell surface in accordance with the present invention. Normally, an epitope will include between about 3-15, generally about 5-15, amino acids. Epitopes of a given protein can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N. J. For example, linear epitopes may be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra.

For purposes of the present invention, antigens can be derived from any of several known viruses, bacteria, parasites and fungi, as well as any of the various tumors. Furthermore, for purposes of the present invention, an "antigen" refers to a protein, which includes modifications, such as deletions, additions and substitutions (generally conservative in nature), to the native sequence, so long as the ability to elicit an immunological response is maintained. These modifications may be deliberate, as through site-directed mutagenesis, or may be accidental, such as through mutations of hosts that produce the antigens.

An "immunological response" or "immune response" is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. Thus, an immunological response as used herein may be one which stimulates the production of cytotoxic T cells, and/or the production or activation of helper T-cells. Such responses can be determined using standard immunoassays and neutralization assays, well known in the art.

Vaccines and immunogenic compositions are both contemplated in connection with the present invention.

By "vertebrate subject" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are intended to be covered.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

B. Formation of Microparticles

In the present invention, a polynucleotide comprising an antigen of interest is adsorbed upon microparticles formed from a polymer and a cationic detergent.

The adsorption of polynucleotides to the surface of the adsorbent microparticles occurs via any bonding-interaction mechanism, including, but not limited to, ionic bonding, hydrogen bonding, covalent bonding, Van der Waals bonding, and bonding through hydrophilic/hydrophobic interactions. Those of ordinary skill in the art may readily select cationic detergents appropriate for the invention. As noted above, known cationic detergents include, but are not limited to, cetyl trimethyl ammonium bromide (CTAB), cetrimide (a mixture consisting chiefly of tetradecyltrimethylammonium bromide, together with smaller amounts of dodecyltrimethylammonium bromide and CTAB), benzalkonium chloride, DDA (dimethyl dioctodecyl ammonium bromide), DOTAP, and the like. CTAB is particularly preferred. Microparticles manufactured with cationic detergents, such as CTAB, e.g., CTAB-PLG microparticles, readily adsorb negatively charged polynucleotides.

Biodegradable polymers for manufacturing microparticles for use with the present invention are readily commercially available from, e.g., Boehringer Ingelheim, Germany and Birmingham Polymers, Inc., Birmingham, Ala. For example, useful polymers for forming the microparticles herein include those derived from polyhydroxybutyric acid; polycaprolactone; polyorthoester; polyanhydride; as well as a poly($\alpha$-hydroxy acid), such as poly(L-lactide), poly(D,L-lactide) (both known as APLA" herein), poly(hydroxybutyrate), copolymers of D,L-lactide and glycolide, such as poly(D,L-lactide-co-glycolide) (designated as "PLG" or "PLGA" herein) or a copolymer of D,L-lactide and caprolactone. Particularly preferred polymers for use herein are PLA and PLG polymers. These polymers are available in a variety of molecular weights, and the appropriate molecular weight for a given use is readily determined by one of skill in the art. Thus, e.g., for PLA, a suitable molecular weight will be on the order of about 2000 to 5000. For PLG, suitable molecular weights will generally range from about 10,000 to about 200,000, preferably about 15,000 to about 150,000, and most preferably about 50,000 to about 100,000.

If a copolymer such as PLG is used to form the microparticles, a variety of lactide:glycolide ratios will find use herein. PLG copolymers with varying lactide:glycolide ratios and molecular weights are readily available commercially from a number of sources including from Boehringer Ingelheim, Germany and Birmingham Polymers, Inc., Birmingham, Ala. These polymers can also be synthesized by simple polycondensation of the lactic acid component using techniques well known in the art, such as described in Tabata et al., *J. Biomed. Mater. Res.* (1988) 22:837-858.

The polynucleotide/microparticles are prepared using any of several methods well known in the art. For example, double emulsion/solvent evaporation techniques, such as those described in U.S. Pat. No. 3,523,907 and Ogawa et al., *Chem. Pharm. Bull.* (1988) 36:1095-1103, can be used herein to make the microparticles.

A water-in-oil-in-water (w/o/w) solvent evaporation system can be used to form the microparticles, as described by O'Hagan et al., *Vaccine* (1993) 11:965-969 and Jeffery et al., *Pharm. Res.* (1993) 10:362. In this technique, the particular polymer is combined with an organic solvent, such as ethyl acetate, dimethylchloride (also called methylene chloride and dichloromethane), acetonitrile, acetone, chloroform, and the like. The polymer will be provided in about a 1-30%, preferably about a 2-15%, more preferably about a 3-10% and most preferably, about a 4% solution, in organic solvent. The polymer solution is emulsified using, e.g., a homogenizer. The emulsion is then optionally combined with a larger volume of an aqueous solution of an emulsion stabilizer such as polyvinyl alcohol (PVA), polyvinyl pyrrolidone, and a detergent, specifically a cationic detergent. The emulsion may be combined with more than one emulsion stabilizer and/or detergent, e.g., a combination of PVA and a cationic detergent. Certain polynucleotides may adsorb more readily to microparticles having a combination of stabilizers and/or detergents. Where an emulsion stabilizer is used, it is typically provided in about a 2-15% solution, more typically about a 4-10% solution. Generally, a weight-to-weight detergent to polymer ratio in the range of from about 0.00001:1 to about 0.1:1 will be used, more preferably from about 0.0001:1 to about 0.01:1, more preferably from about 0.001:1 to about 0.01:1, and even more preferably from about 0.005:1 to about 0.01:1. The mixture is then homogenized to produce a stable w/o/w double emulsion. Organic solvents are then evaporated.

The formulation parameters can be manipulated to allow the preparation of small microparticles on the order of 0.05 μm (50 nm) to larger microparticles 50 μm or even larger. See, e.g., Jeffery et al., *Pharm. Res.* (1993) 10:362-368; McGee et al., *J. Microencap.* (1996). For example, reduced agitation results in larger microparticles, as does an increase in internal phase volume. Small particles are produced by low aqueous phase volumes with high concentrations of emulsion stabilizers.

Microparticles can also be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) The "Wurster Process" in *Controlled Release Technologies: Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst.* (1988) S(2):99-139; and ionic gelation as described by, e.g., Lim et al., *Science* (1980) 210:908-910.

Particle size can be determined by, e.g., laser light scattering, using for example, a spectrometer incorporating a helium-neon laser. Generally, particle size is determined at room temperature and involves multiple analyses of the sample in question (e.g., 5-10 times) to yield an average value for the particle diameter. Particle size is also readily determined using scanning electron microscopy (SEM).

Following preparation, microparticles can be stored as is or freeze-dried for future use.

C. Isolation of Dendritic Cells

Dendritic cells are obtained from any tissue where they reside including non-lymphoid tissues such as the epidermis of the skin (Langerhans cells) and lymphoid tissues such as the spleen, bone marrow, lymph nodes and thymus as well as the circulatory system including blood (blood dendritic cells), for example peripheral blood and cord blood, and lymph (veiled cells).

For example, explants of mouse (Larsen et al., J. Exp. Med. 172:1483-1493 (1990)) or human skin (Richters et al., J. Invest. Dermatol. (1994)) placed in organ culture permit selective migration of dendritic cells into the medium surrounding the explant.

Recent studies have described methods for the isolation and expansion of human dendritic cells, including, from human peripheral blood. (Macatonia et al., 1991, Immunol. 74: 399-406; O'Doherty et al., 1993, J. Exp. Med. 178: 1067-1078 (isolation); and Markowicz et al., 1990, J. Clin. Invest. 85: 955-961; Romani et al., 1994, J. Exp. Med. 180: 83-93; Sallusto et al., 1994, J. Exp. Med. 179: 1109-1118; Berhard et al., 1995, J. Exp. Med. 55: 1099-1104 (expansion)).

Van Tendeloo et al., 1998, Gene Ther. 5: 700-707, discloses techniques for deriving dendritic cells (including Langerhans' cells) from CD34+ progenitor cells obtained from bone marrow and cord blood and from mononuclear cells from peripheral blood.

Dendritic cells may also be treated to induce maturation or activation, e.g., by culturing, preferably in the presence of a specific growth or stimulatory factor or factors. In the examples below, dendritic cells are modified by culturing with GM-CSF.

Additional techniques relating to the preparation of dendritic cells can be found, for example, in U.S. Pat. Nos. 5,788,963, 5,962,318, and 5,851,756, the disclosures of which are herein incorporated by reference.

According to a preferred embodiment of the invention, dendritic cells are obtained from a patient to be treated. The dendritic cells are used to activate T cells of the patient, either in vitro or in vivo, for immunotherapy According to an alternate embodiment, dendritic cells are obtained from a healthy individual. The relevant HLA antigens (both class I and II, e.g., HLA-A, B, C and DR), for example, on the individual's peripheral blood mononuclear cells (PBMC's), are identified and dendritic cells that match the patient, in terms of HLA antigens, are isolated and expanded as described above. For example, in certain instances, a late stage cancer patient who has been treated with radiation and/or chemotherapy agents is not able to provide sufficient or efficient dendritic cells. Thus, dendritic cells from healthy HLA-matched individuals, such as siblings, can be obtained and expanded using any of the methods described above.

D. Antigens

Selected antigens that may be expressed include one or more selected antigens of a vertebrate infectious agent or cancer and can correspond to either structural or non-structural proteins. The invention herein described can provide for association of such antigens with MHC molecules at the surface of dendritic cells such that an immune response to the antigen of interest can be mounted.

For example, the present invention is useful for stimulating an immune response against a wide variety of antigens from the herpes virus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., *Cytomegaloviruses* (J. K. McDougall, ed., Springer-Verlag 1990) pp. 125-169, for a review of the protein coding content of cytomegalovirus; McGeoch et al., *J. Gen. Virol.* (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207-211, for the identification of protein coding sequences in an EBV genome; and Davison and Scott, *J. Gen. Virol.* (1986) 67:1759-1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NSI) and an N-terminal nucleocapsid protein (termed "core") (see, Houghton et al., *Hepatology* (1991) 14:381-388, for a discussion of HCV proteins, including E1 and E2). Each of these proteins, as well as antigenic fragments thereof, will find use in the present composition and methods.

Similarly, the sequence for the δ-antigen from HDV is known (see, e.g., U.S. Pat. No. 5,378,814) and this antigen can also be conveniently used in the present composition and methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines—from the laboratory to license: a case study" in Mackett, M. and Williamson, J. D., Human Vaccines and Vaccination, pp. 159-176, for a discussion of HBV structure; and U.S. Pat. Nos. 4,722,840, 5,098,704, 5,324,513, incorporated herein by reference in their entireties; Beames et al., *J. Virol.* (1995) 69:6833-6838, Birnbaum et al., *J. Virol.* (1990) 64:3319-3330; and Zhou et al., *J. Virol.* (1991) 65:5457-5464.

Antigens derived from other viruses will also find use in the claimed compositions and methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabdoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); *Fundamental Virology*, 2nd Edition (B. N. Fields and D. M. Knipe, eds. 1991), for a description of these and other viruses.

More particularly, the gp120 envelope proteins from any of the above HIV isolates, including members of the various genetic subtypes of HIV, are known and reported (see, e.g., Myers et al., Los Alamos Database, Los Alamos National Laboratory, Los Alamos, N. Mex. (1992); Myers et al., *Human Retroviruses and Aids,* 1990, Los Alamos, N. Mex.: Los Alamos National Laboratory; and Modrow et al., *J. Virol.* (1987) 61:570-578, for a comparison of the envelope sequences of a variety of HIV isolates) and antigens derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol region.

Influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759-767; Webster et al., "Antigenic variation among type A influenza viruses," p. 127-168. In: P. Palese and D. W. Kingsbury (ed.), *Genetics of influenza viruses*. Springer-Verlag, New York). Thus, proteins derived from any of these isolates can also be used in the compositions and methods described herein.

Antigens derived from meningitis A, meningitis B, meningitis C, and other related viruses will also find use in the compositions and methods of the present invention. For examples of meningitis B antigens see, for example, PCT 99/00695 filed Apr. 7, 1999; PCT IB98/01665 filed Oct. 9, 1998 and PCT US99/09346 filed Apr. 30, 1999.

Non-viral organisms that are controlled by T cell immune responses include: pathogenic protozoa (e.g. *Pneumocystis carinii, Trypanosoma, Leishmania, Plasmodia,* and *Toxoplasma gondii*); bacteria (e.g., *Mycobacteria,* and *Legioniella*) and fungi (e.g. *Histoplasma capsulatum* and *Cocidioides immitus*). Hence, antigens derived from these organisms are also useful in connection with the present invention.

Tumor antigens for use in the invention include, but are not limited to, melanoma tumor antigens (Kawakami et al., Proc. Natl. Acad. Sci. USA 91:3515-3519 (1994); Kawakami et al., J. Exp. Med., 180:347-352 (1994); Kawakami et al. Cancer Res. 54:3124-3126 (1994), including MART-1 (Coulie et al., J. Exp. Med. 180:35-42 (1991), gp100 (Wick et al., J. Cutan. Pathol. 4:201-207 (1988) and MAGE antigen, MAGE-1, MAGE-2 and MAGE-3 (Van der Bruggen et al., Science, 254:1643-1647 (1991)); CEA, TRP-1, P-15 and tyrosinase (Brichard et al., J. Exp. Med. 178:489 (1993)); HER-2/neu gene product (U.S. Pat. No. 4,968,603); estrogen receptor, milk fat globulin, p53 tumor suppressor protein (Levine, Ann. Rev. Biochem. 62:623 (1993)); mucin antigens (Taylor-Papdimitriou, International Pub. No. WO90/05142)); telomerases; nuclear matrix proteins; prostatic acid phosphatase; papilloma virus antigens; and antigens associated with the following cancers: melanomas, metastases, adenocarcinoma, thymoma, lymphoma, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, pancreatic cancer and others (e.g., Rosenberg, Ann. Rev. Med. 47:481-91 (1996).

E. Polynucleotides

In accordance with the invention, one or more polynucleotides are inserted ex vivo into dendritic cells, such that one or more selected antigens are presented in effective amounts on the surface of the dendritic cells. By "effective amount" is meant that presentation is sufficient to enable the dendritic cells to provoke an immune response.

Techniques for nucleic acid manipulation are well known. Reagents useful in applying such techniques, such as restriction enzymes and the like, are widely known in the art and commercially available from a number of vendors.

Large amounts of polynucleotide sequences encoding the selected antigens for expression in the dendritic cells of the invention may be obtained using known procedures for molecular cloning and replication of a vector carrying the sequences in a suitable host cell. The nucleic acid sequences for use in the present invention may also be produced in part or in total by chemical synthesis, and may be performed on commercial automated oligonucleotide synthesizers.

Polynucleotides encoding the desired antigens for presentation in the dendritic cells are preferably recombinant expression vectors in which high levels of expression may occur, and which contain appropriate regulatory sequences for transcription and translation of the inserted nucleic acid sequence. The vectors may also contain polynucleotide sequences encoding selected class I and class II MHC molecules, costimulation and other immunoregulatory molecules, ABC transporter proteins, including the TAP1 and TAP2 proteins. Thus, various combinations of polynucleotide sequences may be inserted in a suitable expression vector or vectors. The vector may contain additional elements needed for subsequent replication, such as an origin of replication. The vectors may also contain at least one positive marker that enables the selection of dendritic cells carrying the inserted nucleic acids.

Preferred recombinant expression vectors for the invention include plasmid vectors. Preferred plasmid expression vectors include pCMV (see, for example, U.S. Pat. No. 5,688,688, the entire disclosure of which is hereby incorporated by reference).

Polynucleotides encoding the desired antigen or antigens are introduced into dendritic cells using the transfection methods of the present invention discussed below.

F. Association of Microparticles with Polynucleotides

In order to associate a polynucleotide of interest with a microparticle of interest, microparticles are simply mixed with polynucleotides, for example, in an appropriate buffer solution. The resulting formulation can be lyophilized prior to use. Generally, polynucleotides are added to the microparticles to yield microparticles with adsorbed polynucleotides having a weight-to-weight ratio of from about 0.0001:1 to 0.25:1 polynucleotides to microparticles, preferably, 0.001:1 to 0.1, more preferably 0.01 to 0.05. Polynucleotide content of the microparticles can be determined using standard techniques.

The microparticles of the present invention may have polynucleotides entrapped or encapsulated within them, as well as having polynucleotides adsorbed thereon.

The association of the microparticle with the polynucleotide is referred to alternatively herein as "polynucleotide/microparticles", "transfecting agent" and "transfection agent".

G. Transfection of Dendritic Cells

Once the dendritic cells and polynucleotide/microparticles are prepared, they are incubated in solution for a time and at a temperature sufficient for transfection to occur. According to a preferred embodiment, dendritic cells and polynucleotide/microparticles are incubated for 24 hours at 37° C. in humidified $CO_2$ incubator.

Expression of the polynucleotide of interest after transfection into dendritic cells may be confirmed by immunoassays or biological assays. For example, expression of introduced polynucleotides into cells may be confirmed by detecting the binding to the cells of labeled antibodies specific for the antigens of interest using assays well known in the art such as FACS (Fluorescent Activated Cell Sorting) or ELISA (enzyme-linked immunoabsorbent assay) or by simply by staining (e.g., with (β-gal) and determining cell counts.

T cell activation may be detected by various known methods, including measuring changes in the proliferation of T cells, killing of target cells and secretion of certain regulatory factors, such as lymphokines, expression of mRNA of certain immunoregulatory molecules, or a combination of these.

H. Use of Dendritic Cells to Present Antigen In Vitro and In Vivo

According to an embodiment of the invention, dendritic cells transfected by polynucleotide/microparticles using any of the methods described herein are used to activate T cells in vitro. T cells or a subset of T cells can be obtained from various lymphoid tissues. Such tissues include but are not limited to spleens, lymph nodes, and peripheral blood.

The cells can be co-cultured with transfected dendritic cells as a mixed T cell population or as a purified T cell subset. For instance, it may be desired to culture purified CD8+ T cells with antigen transfected dendritic cells, as early elimination of CD4+ T cells may prevent the overgrowth of CD4+ cells in a mixed culture of both CD8+ and CD4+ T cells. T cell purification may be achieved by positive or negative selection, including but not limited to, the use of antibodies directed to CD2, CD3, CD4, CD5, and CD8. On the other hand, it may be desired to use a mixed population of CD4+ and CD8+ T cells to elicit a specific response encompassing both a cytotoxic and $T_H$ immune response.

After activation in vitro, the T cells are administered to a patient in a dose sufficient to induce or enhance an immune response to the selected antigen expressed by the dendritic cells of the invention.

T cells, as well as dendritic cells as described below, may be introduced into the subject to be treated by using one of a number of methods of administration of therapeutics known in the art. For example, the cells may be administered (with or without adjuvant) parenterally (including, for example, intravenous, intraperitoneal, intramuscular, intradermal, and subcutaneous administration). Alternatively, the cells may be administered locally by direct injection into a tumor or infected tissue. Adjuvants include any known pharmaceutically acceptable carrier. Parenteral vehicles for use as pharmaceutical carriers include sodium chloride solution, Ringer's dextrose, dextrose and sodium chloride, and lactated Ringer's. Other adjuvants may be added as desired such as antimicrobials.

As an example, T cells may be administered, by intravenous infusion, at doses of about $10^8$ to $10^9$ cells/m² of body surface area (see, Ridell et al., 1992, Science 257: 238-241) Infusion can be repeated at desired intervals, for example, monthly. Recipients are monitored during and after T cell infusions for any evidence of adverse effects.

According to a preferred embodiment, the T cells are obtained from the same patient from whom the dendritic cells were obtained.

According to another embodiment, the T cells are obtained from a patient and the dendritic cells, which are used to stimulate the T cells, are obtained from an HLA-matched healthy donor (e.g., a sibling), or vice versa.

According to yet another embodiment, both the T cells and the dendritic cells are obtained from an HLA-matched healthy donor. This embodiment may be particularly advantageous, for example, when the patient is a late stage cancer patient who has been treated with radiation and/or chemotherapy agents and may not be able to provide sufficient or efficient dendritic or T cells.

According to another embodiment of the invention, dendritic cells isolated from a patient are cultured, transfected in vitro and administered back to the patient to stimulate an immune response, including T cell activation. As such, the dendritic cells constitute a vaccine and/or immunotherapeutic agent. As an example, dendritic cells presenting antigen are administered, via intravenous infusion, at a dose of, for example, about $10^6$ to $10^8$ cells. The immune response of the patient can be monitored. Infusion can be repeated at desired intervals based upon the patient's immune response.

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLES

Example 1

Plasmids and DNA formulations. pCMVgag plasmid encoding HIV p55 gag protein under the control of the cytomegalovirus early promoter was purified by ion-exchange chromatography using an Qiagen Endo Free Giga Kit and determined to be endotoxin free (<2.5 EU/ml). For uptake and reporter gene expression experiments, a rhodamine PNA-clamp plasmid encoding B-galactosidase was purchased from Gene Therapy Systems (San Diego, Calif.).

Cationic microparticles were prepared using a modified solvent evaporation process. The microparticles were prepared by emulsifying 10 ml of a 5% w/v polymer (RG 504 PLG (Boehringer Ingelheim)) solution in methylene chloride with 1 ml of PBS (Phosphate-Buffered Saline) at high speed using an IKA homogenizer. The primary emulsion was then added to 50 ml of distilled water containing cetyl trimethyl ammonium bromide (CTAB) (0.5% w/v). This resulted in the formation of a w/o/w emulsion, which was stirred at 6000 rpm for 12 hours at room temperature, allowing the methylene chloride to evaporate. The resulting microparticles were washed twice in distilled water by centrifugation at 10,000 g and freeze dried.

Plasmid DNA was adsorbed onto the microparticles targeting a 1% w/w load (by incubating 100 mg of cationic microparticles in a 1 mg/ml solution of DNA at 4° C. for 6 hours). The particles were separated by centrifugation, washed with TE buffer and lyophilized until use. The size distribution of the PLG-CTAB microparticles was determined using a particle size analyzer (Malvern Instruments, U.K.); formulations utilized in this study had a mean size of approximately 1 µm. Without wishing to be held to any particular theory of operation, the use of the cationic surfactant is believed to result in a net surface positive charge for the adsorption of rhodamine-labeled plasmid DNA. Actual DNA load was quantified by assaying free DNA content in the supernatant and subtracting from total input DNA. PLG-CTAB-DNA formulations utilized in this example had an actual DNA load ranging from 0.64-0.81% (w/w).

Cell culture. All cells used in this study were cultured in RPMI-1640 (BioWhittaker) supplemented with 10% heat-inactivated FBS, 2 mM glutamine, 100 U/ml penicillin, 100 n/ml streptomycin, and 0.05 mM 2-mercaptoethanol at 37° C. in a humidified 7% $CO_2$ incubator. The murine T cell hybridoma 12.2 is an MHC class I, d-restricted line which recognizes the p7g peptide of HIV gag protein (provided by Gillis Otten, Chiron Corp.)

Bone marrow isolation. Female Balb/c mice, 6-8 weeks old, were obtained from Charles River Laboratories (Holister, Calif.). Bone marrow was flushed from the femurs and tibia, washed and frozen (-80° C.) in heat-inactivated fetal bovine serum supplemented with 10% cell-culture grade DMSO (dimethyl sulfoxide) at a density of $2 \times 10^7$ cells/ml.

Generation of bone-marrow-derived dendritic cells (BM-DCs). Frozen cell aliquots were rapidly thawed and washed to remove DMSO. Cells were plated in 150 mm suspension culture dishes containing 20 ml supplemented RPMI (see above) with the addition of 200 units/ml murine GM-CSF (Preprotech). On day 3 of culture, cells were again supplemented with murine GM-CSF, and on day 5, one-half of the culture volume was centrifuged to replace fresh medium containing GM-CSF. BMDCs were harvested by gentle pipetting. Unless otherwise indicated, bone marrow derived dendritic cells were incubated with the gene-encoding antigen on day 6 and incubated 24 h further. BMDCs were analyzed for cell surface markers by FACS (fluorescence-activated cell sorter) and were characterized as immature by staining positive for CD11c, CD11b, H-dK$^d$, I-A$^{d(low)}$, CD80$^{(low)}$, and CD86$^{(low)}$ (PharMingen).

Cellular uptake and fluorescence microscopy. BMDCs were plated at a density of $1 \times 10^6$ cells in 2 ml medium in 6-well culture dishes. Rhodamine-labelled DNA in the form of naked plasmid or formulated on PLG-CTAB microparticles was added to the wells at 1 µg DNA/ml. Following overnight incubation, cells were washed and applied to Superfrost microscope slides (Fisher Scientific) by cytospin (4000 rpm×5 min). Slides were air-dried, mounted in Vectashield (Vector, Burlingame, Calif.) and visualized using a Zeiss Axiophot fluorescence microscope with rhodamine filters (Chroma, Brattleboro, Vt.). Images were documented on Kodak EliteChrome film (100 ASA) and scanned into Adobe Photoshop.

Naked plasmid DNA was readily internalized into punctate arrangements suggestive of endosomes. In contrast, the cellular distribution of rhodamine-labeled plasmid DNA formulated on PLG-CTAB-DNA microparticles suggested a more diffuse distribution of the rhodamine signal. Similar patterns of internalization have been observed with DiI-labeled microparticles as well as PLG-CTAB microparticles containing encapsulated FITC-labeled bovine serum albumin. Without wishing to be held to any particular theory, it appears as though the cationic surfactant may disrupt the endosomal compartment allowing DNA localization to the nucleus.

Example 2

RNA isolation and RT-PCR. BMDCs were plated at a density of $0.5 \times 10^6$ cells/ml in RPMI+GM-CSF on day 6 of culture. Cells were either left untreated as negative control, or incubated in the presence of 1 µg/ml pCMV-gag DNA either alone (naked) or formulated on PLG-CTAB microspheres. Following 24 h incubation, $2 \times 10^5$ cells were removed, washed 2× in cold PBS (Life Technologies), then lysed per manufacturer's instructions for the mRNA Capture kit (Roche) and frozen at -80° C. Samples were thawed on ice with the addition of RNase-free DNase and RNase inhibitor (Roche). The mRNA isolation protocol was then followed for isolation of biotin-hybridized mRNA in streptavidin PCR tubes. The Promega Reverse Transcription System (Madison, Wis.) was utilized for cDNA synthesis according to manufacturer's instructions, and the reaction was run at 45° C. for 45 min, followed by heat inactivation at 99° C. for 5 min. PCR control tubes were treated as stated above but without the addition of AMV-reverse transcriptase for subsequent determination of the presence of contaminating plasmid DNA. For PCR amplification, samples were set up to amplify a 300 bp region of the HIV gag gene, or B-actin as a positive control using general PCR conditions.

Products were analyzed by agarose gel electrophoresis (FIG. 1). Lane designations are as follows: 1) 500 bp DNA ladder, 2-4) β-actin control RT-PCR reactions from untreated, plasmid DNA treated, and PLG-CTAB-DNA treated BMDCs, 5) 100 bp DNA ladder, 6) untreated mRNA prep with control spike of pCMV-gag DNA, 8-10) p55gag RT-PCR from untreated, plasmid DNA treated, and PLG-CTAB-DNA treated BMDCs, 11-13) PCR negative control from untreated, plasmid DNA treated, and PLG-CTAB-DNA treated BMDCs, 14) pCMV-gag DNA PCR positive control. As illustrated in FIG. 1, the gene product was only detected by RT-PCR in PLG-CTAB-DNA preparations, and was not the result of plasmid DNA contamination in the mRNA preparation as shown by the control PCR-only reactions. Hence, PLG-CTAB-DNA microparticles facilitate gene expression in BMDC. It is of interest to note, however, that unsuccessful attempts were made to detect reporter gene products, both luciferase and β-galactosidase, in BMDC cell lysates by luminometer and colorimetric substrate respectively.

Example 3

Stimulation of T cells. Bone marrow cells differentiated in the presence of GM-CSF for 6 days were classified as immature as determined by FACS analysis of cell surface phenotype $CD11c^+$, $CD11b^+$, $H-dK^{d+}$, $I-A^{d(low)}$, $CD80^{(low)}$, and $CD86^{(low)}$, and mature by day 9 ($CD11c^+$, $CD11b^+$, $H-2K^{d+}$, $I-A^{d(bright)}$, $CD80^+$, $CD86^+$) (R. C. Fields, J. J. O., J. A. Fuller, E. K. Thomas, P. J. Geraghty, and J. J. Mule'. 1998. Comparative analysis of murine dendritic cells derived from spleen and bone marrow. *J. Immunother.* 21:323). Both immature and mature BMDCs were stimulated for 24 h with PLG-CTAB-pCMVgag DNA or naked pCMVgag DNA. Controls included untreated cells, microparticles alone or formulated with non-specific plasmid DNA (pCMV-luciferase) as well as non-specific naked DNA. T cell hybridoma 12.2 (a d-restricted T cell hybridoma specific for the p7g epitope (AMQMLKETI) of HIV p55 gag) was plated at $1\times10^5$ cells per well of a 96 well, U-bottom microtiter plates. Varying numbers of BMDCs were plated with the hybridoma in a total culture volume of 2004 Each individual experiment was performed in duplicate. After a 24 h culture period, the plates were centrifuged and the supernatants were removed and stored at −80° C. until further assay for IL-2 production. To assay for levels of IL-2 secreted into the medium, culture supernatants were thawed at room temperature and plated on pre-treated mouse IL-2 ELISA microtiter plates and analyzed per manufacturer's instructions (Endogen). Following development of colorimetric substrate, microtiter plates were read by a Molecular Devices vmax kinetic plate reader and analyzed with SoftMax software.

Figure 2:
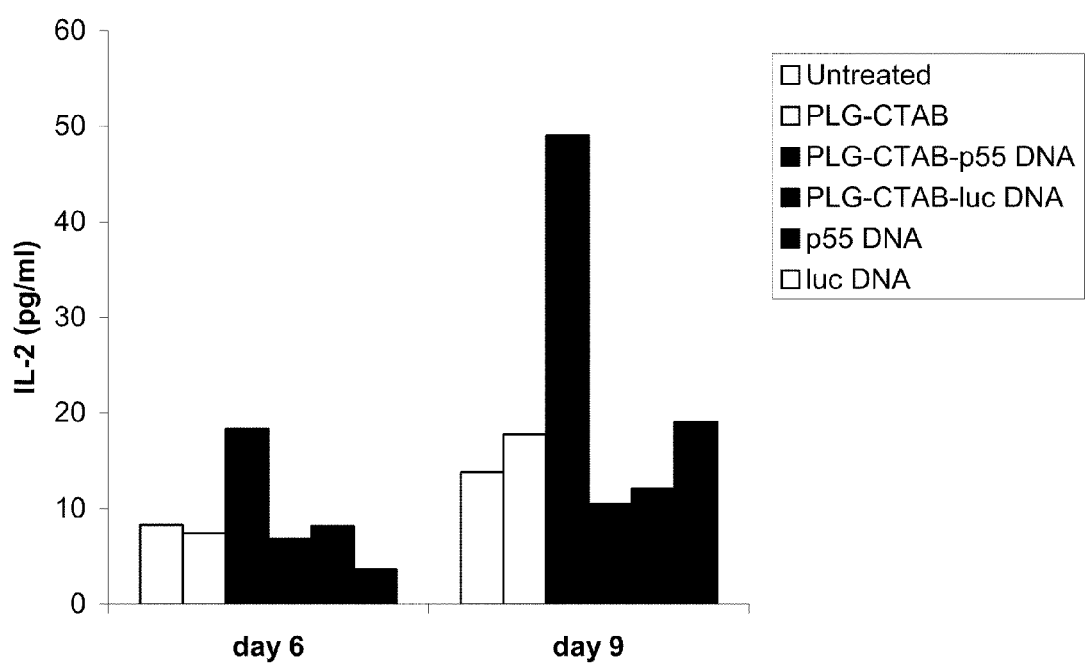
FIG. 2 illustrates IL-2 production level after stimulation of an MHC class I T cell hybridoma with bone-marrow-derived dendritic cells (BMDCs). Both immature (6 day) and mature (9 day) BMDCs were examined. BMDC treatment within each maturity group is as follows (from left to right): untreated, treatment with PLG-CTAB, treatment with PLG-CTAB-pCMVgag DNA, treatment with PLG-CTAB-luc DNA, treatment with naked pCMVgag DNA, and treatment with naked luc DNA.

As shown in FIG. 2, only PLG-CTAB-pCMV-gag treated BMDCs stimulated levels of IL-2 production above background. It is interesting to note that immature cells thought to be efficient at antigen internalization resulted in IL-2 levels that were 55% greater than background levels whereas more mature BMDCs, which express higher levels of MHC molecules on their cell surfaces, and are believed to be more efficient at antigen presentation resulted in IL-2 levels 77% greater than background. Furthermore, PLG-CTAB-DNA-mediated stimulation of IL-2 production is dependent on the presence of antigen presenting cells, as the hybridoma alone treated with PLG-CTAB-DNA did not result in detectable levels of IL-2 as determined by ELISA. Naked DNA in the presence of free CTAB also did not result in antigen presentation. Although PLG-CTAB-DNA treatment resulted in transfection of dendritic cells in vitro, IL-2 production was two orders of magnitude less than that observed via a viral technique, i.e., with a recombinant vaccinia virus expressing the gag gene.

In addition to being antigen specific to a d-restricted epitope of the HIV p55gag antigen, the T cell hybridoma utilized in this study was generated using the lacZ-inducible BWZ.36 fusion partner (provided by N. Shastri, U. of California Berkeley) which contains the *Escherichia coli* lacZ reporter gene under the control of the nuclear factor of activated T cells (NFAT) enhancer element of the IL-2 gene (Shastri, S. S. et al. 1994. LacZ inducible, antigen/MHC-specific T cell hybrids. *Intl. Immunol.* 6:396). To confirm the results obtained by IL-2 ELISA, we also assayed the hybridoma cells by colorimetric assay for B-galactosidase (β-galactosidase staining kit, Invitrogen). Representative cell counts from microscope fields of view indicate a significant increase of blue-stained cells over background in PLG-CTAB-pCMVgag-treated BMDCs (average counts 29 vs. 128 respectively).

The stimulation of IL-2 production by T cell recognition of antigen presented in the context of MHC class 1 molecules was found to be time-dependent. Experiments (data not included) have shown that levels of IL-2 production eventually decrease over time. However, significant levels of IL-2 are produced after 7 days (about 15% of the 24-hour IL-2 production level).

Figure 3:
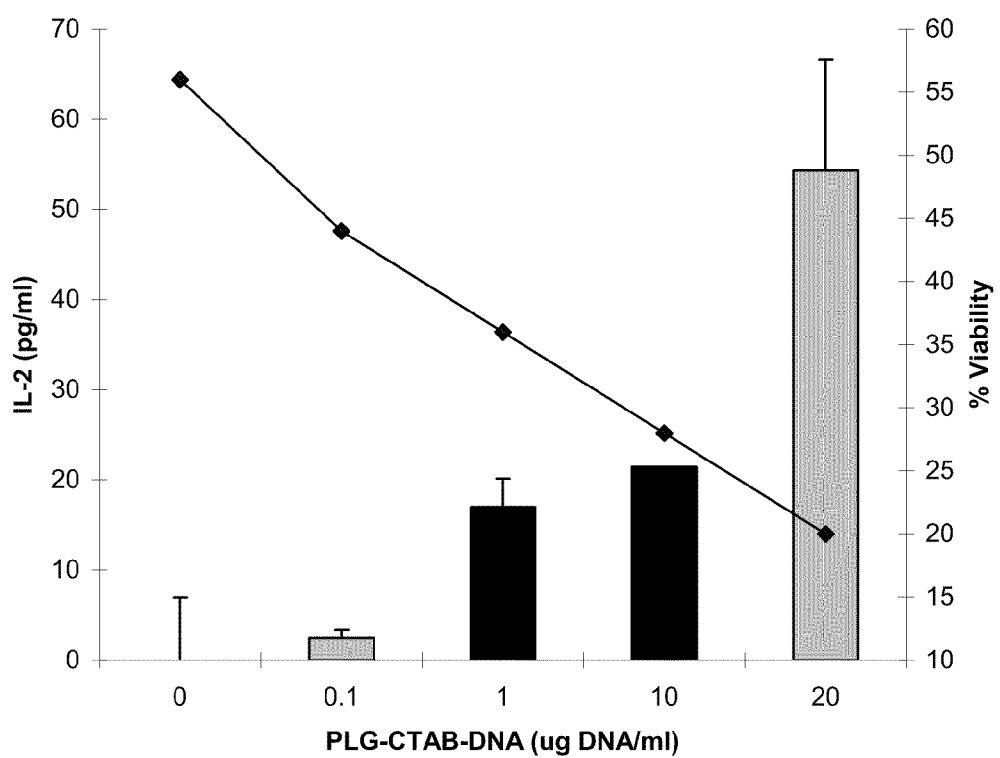
FIG. 3 illustrates IL-2 production level after stimulation of T cell hybridoma (left y-axis, bar series) with BMDCs that were incubated with varying concentrations of pCMV-gag plasmid DNA formulated on PLG-CTAB microparticles.

The stimulation of IL-2 production by T cell recognition of antigen presented in the context of MHC class 1 molecules was found to be dose-dependent. In FIG. 3, levels of IL-2 production increase with the dose presented to BMDCs; however it is of interest to note the corresponding increase in toxicity (lower % viability) that is also observed. However, this deleterious effect may be abrogated by the apparent adjuvant activity of PLG-CTAB-DNA formulation.

Figure 4:
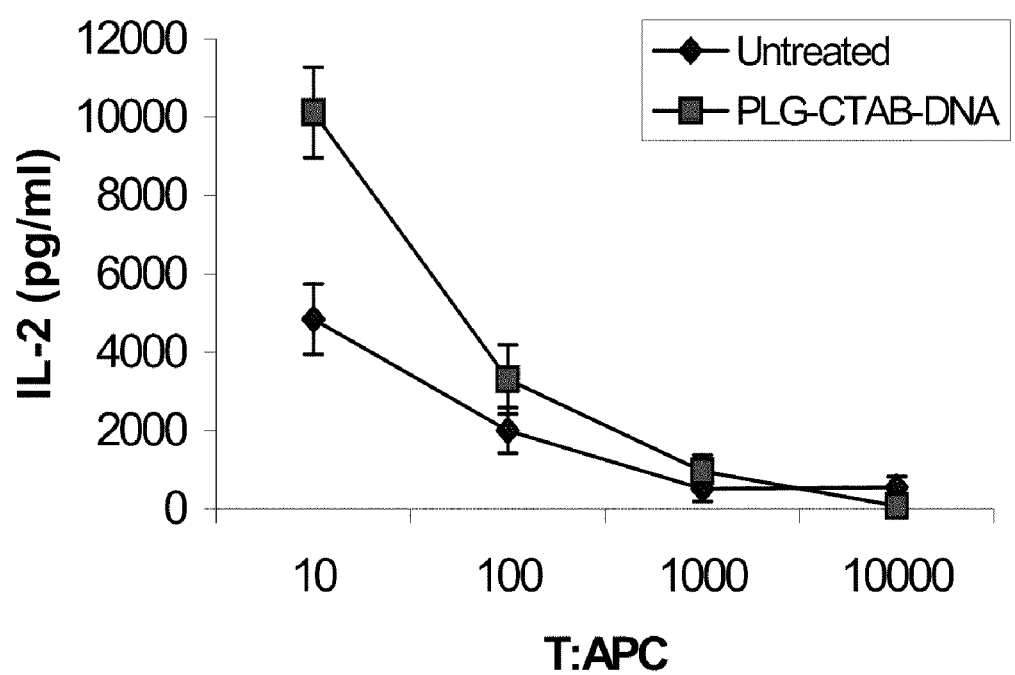
FIG. 4 illustrates IL-2 production level after stimulation of gag-specific T cell hybridoma with either naïve (untreated) BMDCs or BMDCs treated with PLG-CTAB-pCMVgag DNA, and after pulsing with an excess of synthetic peptide epitope. Varying ratios of T cells to antigen presenting cells (i.e., BMDCs) were studied, with the number of T cells being held constant in all cases. Data points represent the mean±error of duplicate samples assayed by a series of dilutions.

As shown in FIG. 4, naïve BMDCs and BMDCs treated with PLG-CTAB-pCMVgag DNA were pulsed with an excess of synthetic p7g peptide epitope (1 ng/ml) and serially diluted and plated with $1\times10^5$ gag-specific MHC class I T hybridoma cells. Hence, various T cell to antigen presenting cell ratios were provided, with the number of T cells being held constant. Stimulation was determined by IL-2 ELISA. As seen in FIG. 4, such treated cells become more efficient at T cell stimulation than untreated cells. Stimulation of IL-2 production by the T cell hybridoma was dose dependent and detectable down to a T:APC ratio of 10000:1. Although pulsing surface MHC class I molecules with synthetic peptide epitope was shown to be highly efficient at stimulating the T cell response, even in untreated BMDCs, this is not expected to be a feasible approach to genetic immunotherapy due to the polymorphism of MHC class I epitopes in an outbred population. These data do however demonstrate upregulation of MHC class I on the dendritic cell surface, a partial indication of activation by the PLG/CTAB formulation. This activation is expected to significantly increase the effectiveness of passively transferred dendritic cells transfected by the process of the invention.

As seen from the above, PLG-CTAB-DNA microparticles can be efficiently internalized by dendritic cells. Without wishing to be held to any particular theory, the presence of the cationic surfactants on the surface may contribute to endosome disruption and cytoplasmic or nuclear localization. Gene expression was also observed by reverse-transcriptase PCR, indicating direct transfection of BMDCs in vitro. To exploit the potent antigen uptake and presentation capabilities of dendritic cells, it was of interest to determine whether expressed antigen can be processed and presented on MHC molecules. It was seen that BMDCs incubated with PLG-CTAB microparticles formulated with pCMVgag plasmid encoding the HIV gag protein specifically stimulate antigen-specific T cell hybridoma, resulting in the production of IL-2. Moreover, it has been shown that such microparticles allow greater transfection than unmodified plasmid DNA, using the T cell hybridoma-based readout. It has also been demonstrated that pulsing of dendritic cells with PLG-CTAB-DNA is an effective mechanism for rapid internalization, target gene expression, and antigen presentation in vitro.

Although preferred embodiments of the subject invention have been described in some detail, it is understood that obvious variations can be made without departing from the spirit and the scope of the invention as defined by the appended claims.

The invention claimed is:

1. A method for producing an immune response in a vertebrate subject in need thereof comprising:
    activating T cells by subjecting them to dendritic cells produced by a method that comprises incubating the dendritic cells and a transfection agent for a time sufficient to transfect the dendritic cells with the polynucleotide, said transfection agent comprising a polynucleotide that encodes an antigen associated with a virus or a tumor adsorbed on microparticles comprised of a biodegradable polymer and a cationic detergent, wherein polynucleotide is not entrapped within said microparticles;
    administering said activated T cells to said subject.

2. The method according to claim 1, in which the dendritic cells and T cells originate from the vertebrate subject.

3. The method according to claim 1, in which the dendritic cells and T cells originate from a healthy vertebrate subject MHC-matched to the vertebrate subject.

4. The method according to claim 1, in which the T cells are administered parenterally.

5. The method according to claim 1, in which the T cells are administered by direct injection into affected tissue.

* * * * *